United States Patent
Rahman et al.

(10) Patent No.: US 10,597,734 B2
(45) Date of Patent: Mar. 24, 2020

(54) **GENETIC MARKERS FOR DIAGNOSIS OF TUBERCULOSIS CAUSED BY *MYCOBACTERIUM TUBERCULOSIS***

(71) Applicants: KUSUMA SCHOOL OF BIOLOGICAL SCIENCES, New Delhi (IN); EUROPEAN MOLECULAR BIOLOGY LABORATORY, Heidelberg (DE)

(72) Inventors: Syed Asad Rahman, Cambridge (GB); Javeed Ahmad, New Delhi (IN); Nasreen Z Ehtesham, New Delhi (IN); Seyed E Hasnain, New Delhi (IN)

(73) Assignees: EUROPEAN MOLECULAR BIOLOGY LABORATORY, Heidelberg (DE); KUSUMA SCHOOL OF BIOLOGICAL SCIENCES INDIAN INSTITUTE OF TECHNOLOGY, New Delhi (IN)

( * ) Notice: Subject to any disclaimer, the term of this patent is extended or adjusted under 35 U.S.C. 154(b) by 266 days.

(21) Appl. No.: 15/100,850

(22) PCT Filed: Dec. 1, 2014

(86) PCT No.: PCT/IB2014/066469
§ 371 (c)(1),
(2) Date: Jun. 1, 2016

(87) PCT Pub. No.: WO2015/083056
PCT Pub. Date: Jun. 11, 2015

(65) Prior Publication Data
US 2016/0355872 A1    Dec. 8, 2016

(30) Foreign Application Priority Data

Dec. 3, 2013    (IN) .......................... 5572/CHE/2013

(51) Int. Cl.
*C07H 21/04*    (2006.01)
*C12Q 1/68*    (2018.01)
*C12Q 1/689*    (2018.01)
*C12Q 1/6883*    (2018.01)

(52) U.S. Cl.
CPC ........... *C12Q 1/689* (2013.01); *C12Q 1/6883* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 6,183,957 B1 * | 2/2001 | Cole | ..................... C07K 14/35 435/6.15 |
| 6,294,328 B1 | 9/2001 | Fleischmann et al. | |
| 2003/0135026 A1 | 7/2003 | Reed et al. | |

* cited by examiner

*Primary Examiner* — Jeanine A Goldberg
(74) *Attorney, Agent, or Firm* — McDonnell Boehnen Hulbert & Berghoff LLP

(57) ABSTRACT

The application is related to novel signature sequences for diagnosis of *Mycobacterium tuberculosis* in clinical samples with 100% specificity and a very high degree of sensitivity.

4 Claims, 3 Drawing Sheets

Specification includes a Sequence Listing.

Fig. 1A

M: 100bp DNA ladder

Fig. 1B

M: 100bp DNA ladder

Fig. 1C

M: 100bp DNA ladder

Fig. 1D

M: 100bp DNA ladder

Fig. 2

M: 100bp DNA ladder

Fig. 3

Lane M: 100bp DNA Ladder

Lane 1: Positive control (genomic DNA as template)

Lane 2: Rv1507A (patient1)

Lane 3: Rv1954A (patient2)

Lane 4: Rv1954a (Patient3)

Lane 5: Rv1509 (patient1)

SEQUENCE LISTING

<160> NUMBER OF SEQ ID NOS: 14

<210> SEQ ID NO 1
<211> LENGTH: 230
<212> TYPE: DNA
<213> ORGANISM: Mycobacterium tuberculosis

<400> SEQUENCE: 1
atgcaatcag gtcaaaatat cctcgccaag gtatgtaatt tgattgaaca atcgcgactt    60

| tcttcaacgc ggtgtctcca atttagaata acaaatacgt cgcgcccgcg acagctccgc | 120 |
| tggagcgagt tcaagcgatt ctgcgacata ttcaatatgg tgctcgggaa ggccaggatg | 180 |
| ggccgcgacc cggggcgtcc ggtgcgcgat gaacgtcgca tcgtctcctg | 230 |

<210> SEQ ID NO 2
<211> LENGTH: 330
<212> TYPE: DNA
<213> ORGANISM: Mycobacterium tuberculosis

<400> SEQUENCE: 2

| gtgtttgcgt tgagtaataa tctgaaccgt gtgaacgcat gcatggatgg attccttgcc | 60 |
| cgtatccgct cacatgttga tgcgcacgcg ccagaattgc gttcactgtt cgatacgatg | 120 |
| gcggccgagg cccgatttgc acgcgactgg ctgtccgagg acctcgcgcg gttgcctgtc | 180 |
| ggtgcagcat tgctggaagt gggcgggggg gtacttctgc tcagctgtca actggcggcg | 240 |
| gagggatttg acatcaccgc catcgagccg acgggtgaag gttttggcaa gttcagacag | 300 |
| cttggcgaca tcgtgctgga attggctgca | 330 |

<210> SEQ ID NO 3
<211> LENGTH: 280
<212> TYPE: DNA
<213> ORGANISM: Mycobacterium tuberculosis

<400> SEQUENCE: 3

| atggccaggg gcagggtcgt gtgcattggg gatgcaggtt gcgactgtac acccggcgtg | 60 |
| ttccgcgcga cagcgggtgg gatgccggtg ctggtggtca tcgagtctgg gacaggaggt | 120 |
| gatcagatgg ctcgtaaagc tacgtccccg ggtaagccgg ctccgacgtc gggacagtat | 180 |
| cgcccggttg gcggtggcaa cgaggtgacc gttccgaagg acaccgtct gcctccctcg | 240 |
| cccaagcccg gtcagaagtg ggtgaacgtc gatccgacga | 280 |

<210> SEQ ID NO 4
<211> LENGTH: 390
<212> TYPE: DNA
<213> ORGANISM: Mycobacterium tuberculosis
<220> FEATURE:
<221> NAME/KEY: misc_feature
<222> LOCATION: (390)..(390)
<223> OTHER INFORMATION: optionally absent

<400> SEQUENCE: 4

| ttgaccatgg cgtgtaccgc gtgcccgacg atttggacgc tccgttgtca gacgacgtgc | 60 |
| tcgaacgctt tcaccggtga agcgctacct catcgacacc cacgtttggc tgcggatgcc | 120 |
| gtcaacgaaa cacgggcgat tgttcaggac gtccgcaaca gcattctctt gtcggccgcc | 180 |
| agtgcctggg agatcgcgat caactaccgc ctcggcaagc tcccgccgcc cgagccatcg | 240 |
| gcctcttacg tgcccgatcg aatgcgccgc tgcggcacgt cgccgctgtc agttgaccac | 300 |
| gcacacactg cgcaccgcag agcttccgga tcaccatcga catccattcg accgtgtgct | 360 |
| catcgcccag gcacagctgc ttggcctgac | 390 |

<210> SEQ ID NO 5
<211> LENGTH: 25
<212> TYPE: DNA
<213> ORGANISM: Mycobacterium tuberculosis

<400> SEQUENCE: 5

```
atgcaggttg cgactgtaca cccgg                                          25
```

```
<210> SEQ ID NO 6
<211> LENGTH: 24
<212> TYPE: DNA
<213> ORGANISM: Mycobacterium tuberculosis

<400> SEQUENCE: 6
taggctgctt cttgttctcg ccgg                                           24

<210> SEQ ID NO 7
<211> LENGTH: 32
<212> TYPE: DNA
<213> ORGANISM: Mycobacterium tuberculosis

<400> SEQUENCE: 7
gtgtttgcgt tgagtaataa tctgaaccgt gt                                  32

<210> SEQ ID NO 8
<211> LENGTH: 24
<212> TYPE: DNA
<213> ORGANISM: Mycobacterium tuberculosis

<400> SEQUENCE: 8
ccgctgtagc acgaccttaa ccga                                           24

<210> SEQ ID NO 9
<211> LENGTH: 503
<212> TYPE: DNA
<213> ORGANISM: Mycobacterium tuberculosis

<400> SEQUENCE: 9
atgcaatcag gtcaaaatat cctcgccaag gtatgtaatt tgattgaaca atcgcgactt    60
tcttcaacgc ggtgtctcca atttagaata caaatacgt cgcgcccgcg acagctccgc   120
tggagcgagt tcaagcgatt ctgcgacata ttcaatatgg tgctcgggaa ggccaggatg   180
ggccgcgacc cggggcgtcc ggtgcgcgat gaacgtcgca tcgtctcctg tgagataatt   240
gcatccgatc atatagggct ggctgcggct aggttgctgg caaaaagata tcgcggccga   300
tccgtttctg gttttgtctt gatgatcaaa tccgcttccg ttcacgagat cgattcctgg   360 tcttcccccca gcgtcgcgat gtcgataggt gtcgcgcttt gttcgtaccc gcactacgcg   420
gcggcgagaa cctcgccacc gaatcgggat tgggggggagg ataccactcg gtcgaggccc   480
gtcaccggcc ttctagcggg ttg                                           503

<210> SEQ ID NO 10
<211> LENGTH: 882
<212> TYPE: DNA
<213> ORGANISM: Mycobacterium tuberculosis

<400> SEQUENCE: 10
gtgtttgcgt tgagtaataa tctgaaccgt gtgaacgcat gcatggatgg attccttgcc    60
cgtatccgct cacatgttga tgcgcacgcg ccagaattgc gttcactgtt cgatacgatg   120
gcggccgagg cccgatttgc acgcgactgg ctgtccgagg acctcgcgcg gttgcctgtc   180
ggtgcagcat tgctggaagt gggcgggggg gtacttctgc tcagctgtca actggcggcg   240
gagggatttg acatcaccgc catcgagccg acgggtgaag ttttggcaa gttcagacag   300 cttggcgaca tcgtgctgga attggctgca gcacgaccca ccatcgcgcc atgcaaggcg   360
gaagacttta tttccgagaa gcggttcgac ttcgccttct cgctgaatgt gatggagcac   420
```

```
atcgaccttc cggatgaggc agtcaggcgg gtatcggaag tgctgaaacc gggggccagt    480
taccacttcc tgtgcccgaa ttacgtattc ccgtacgaac cgcatttcaa tatcccaaca    540
ttcttcacca aagagctgac atgccgggtg atgcgacatc gcatcgaggg caatacgggc    600
atggatgacc cgaagggagt ctggcgttcg ctcaactgga ttacggttcc caaggtgaaa    660
cgctttgcgg cgaaggatgc gacgctgacc ttgcgcttcc accgtgcaat gttggtatgg    720
atgctggaac gcgcgctgac ggataaggaa ttcgctggtc gccgggcaca atggatggtc    780
gctgctattc gctcggcggt gaaattgcgt gtgcatcatc tggcaggcta tgttcccgct    840
acgctgcagc ccatcatgga tgtgcggcta acgaagaggt aa                      882

<210> SEQ ID NO 11
<211> LENGTH: 23
<212> TYPE: DNA
<213> ORGANISM: Mycobacterium tuberculosis

<400> SEQUENCE: 11
tgtaccgcgt gcccgacgat ttg                                            23

<210> SEQ ID NO 12
<211> LENGTH: 23
<212> TYPE: DNA
<213> ORGANISM: Mycobacterium tuberculosis

<400> SEQUENCE: 12
acaggcagct aacagggcgt cgg                                            23

<210> SEQ ID NO 13
<211> LENGTH: 393
<212> TYPE: DNA
<213> ORGANISM: Mycobacterium tuberculosis

<400> SEQUENCE: 13
tggtataagc tggttttaga cgaaaaggac cccacctcgg ggtctgatgg ccaggggcag    60
ggtcgtgtgc attggggatg caggttgcga ctgtacaccc ggcgtgttcc gcgcgacagc    120
gggtgggatg ccggtgctgg tggtcatcga gtctgggaca ggaggtgatc agatggctcg    180
taaagctacg tcccccggta agccggctcc gacgtcggga cagtatcgcc cggttggcgg    240
tggcaacgag gtgaccgttc cgaagggaca ccgtctgcct ccctcgccca agcccggtca    300
gaagtgggtg aacgtcgatc cgacgaagaa caagagcggc cgcggctgag cttgtgccgt    360
cgggatgggt gtcgcaccgt ctcggcgggt cgc                                 393

<210> SEQ ID NO 14
<211> LENGTH: 553
<212> TYPE: DNA
<213> ORGANISM: Mycobacterium tuberculosis

<400> SEQUENCE: 14
gccgcggcga gccggtagca aagcttgtgc cgctgcatcc tcatgagact cggcggttag    60
gcattgacca tggcgtgtac cgcgtgcccg acgatttgga cgctccgttg tcagacgacg    120
tgctcgaacg ctttcaccgg tgaagcgcta cctcatcgac accacgtttt ggctgcggat    180
gccgtcaacg aaaacgggc gattgttcag gacgtccgca acagcattct cttgtcggcc    240
gccagtgcct gggagatcgc gatcaactac cgcctcggca agctcccgcc gcccgagcca    300
tcggcctctt acgtgcccga tcgaatgcgc cgctgcggca cgtcgccgct gtcagttgac    360
```

-continued

```
cacgcacaca ctgcgcaccg cagagcttcc ggatcaccat cgacatccat tcgaccgtgt    420
gctcatcgcc caggcacagc tgcttggcct gacgatcatc accgccgacg ccctgttagc    480
tgcctgtgat gtcgcggttg tcgccgcgta gacaacgcgt cggcggtgct ctggattctt    540
ggcccgcaca ccg                                                      553
```

GENETIC MARKERS FOR DIAGNOSIS OF TUBERCULOSIS CAUSED BY *MYCOBACTERIUM TUBERCULOSIS*

RELATED APPLICATION

This application claims priority to International Patent Application No. PCT/IB2014/066469, filed Dec. 1, 2014, which claims priority to Indian Patent Application No. 5572/CHE/2013, filed Dec. 3, 2013, both of which are hereby incorporated herein by reference in their entireties.

FIELD OF THE INVENTION

The application is related to novel signature sequences for diagnosis of *Mycobacterium tuberculosis* in clinical samples. These signature sequences have the ability to differentiate *Mycobacterium tuberculosis* DNA from other mycobacterial species by PCR with 100% specificity and very high sensitivity.

BACKGROUND OF THE INVENTION

Tuberculosis (TB) is a major global health problem with an alarming rate of mortality associated with it. It is one of the leading infectious diseases caused by bacteria taking one human life every 15-20 seconds globally. Estimates of 2011 reveal that there are almost 9 million new cases and 1.4 million TB deaths (Global Tuberculosis Report 2012, WHO 2013). The disease is caused by *Mycobacterium tuberculosis*, a member of the genus *Mycobacterium*, while in a few cases *Mycobacterium bovis* has been reported to be the causal organism. More than 100 *mycobacterium* species are known and among them only a few are pathogenic for humans.

Conventional diagnostic methods include examination of sputum smear under a microscope for acid-fast mycobacteria and radiological reading of lungs. However, in most cases the sputum smear examination turns out to be negative for the bacteria due to early stages of infection and lung changes are not readily visible on an x-rays until several months into the infection.

Diagnosis of mycobacteria-related disease poses difficulties for several reasons which have been recognized by researchers and clinicians over the years. Firstly, these bacteria are in small numbers and are already at a contagious stage when they become detectable by conventional methods. Pulmonary disease caused by different mycobacteria are not readily detectable clinically or radiologically. Detection of organism in culture achieves 100% specificity but the growth of mycobacteria in culture takes about 3-6 weeks (Bates et al, Am. Respir. 134, 415-417, 1986) thus making the process time-consuming. In addition, repeated cultures may be required to ensure success.

Several molecular tests for tuberculosis have been developed in the past. These include the Gen-probe 'Amplified *mycobacterium* direct test' by Abbe et al (J. Clin. Mincrobiol. 31, 3270, 1993), ligase chain reaction (LCR) (J. Clin. Microbiol. 35, 2424, 1997), PCR based Roche Amplicor TB test (J. Clin. Microbiol. 33, 1832, 1995) and IS6110 based detection (J. Clin. Microbiol. 28, 2668, 1990).

U.S. Pat. No. 5,168,039 discloses the IS6110 based detection of *M. tuberculosis* wherein a repetitive DNA segment specific for members of *M. tuberculosis* complex is used for the diagnosis. While IS6110 based detection system has been shown to have high level of specificity, there are also reports on false positive detections of 3 to 20% making it unreliable (J. Clin. Microbiol. 32, 277, 1994). In addition, lack of IS6110 sequence in some *M. tuberculosis* strains may also limit the use of the same for diagnostic tests routinely (Tuber. Lung Dis. 76, 550, 1995). U.S. Pat. No. 7,638,309 provides detection of mycobacteria in clinical specimens in the intergenic region between methyl mycotic acid synthase genes mmaA1 and mmaA2 and the flanking region in mmaA1 and mmaA2 genes.

Thus, it appears that there is a paucity of simple, rapid and reliable tests that can specifically detect *M. tuberculosis* during early stages of the disease. The present invention has identified 'signature sequences' that can differentiate *M. tuberculosis* from a are number of other mycobacterial DNA. These 'signature sequences' are used in detection of early disease in clinical samples of patients.

SUMMARY OF THE INVENTION

The invention provides novel signature sequences for diagnosis of *Mycobacterium* species (sps) in clinical samples with 100% specificity and a very high degree of sensitivity.

In one aspect, the invention provides a nucleotide sequence capable of selectively detecting pathogenic *Mycobacterium* sps using oligonucleotide primers corresponding to the signature sequence selected from SEQ ID NO: 1, 2, 3 or 4.

In another aspect the invention provides a method of detecting pathogenic *mycobacterium* sps in a clinical sample, said method comprising the steps of:

a. removal of contaminants from the clinical sample by conventional methods;

b. extraction of genomic DNA from the contaminant-free clinical sample;

c. designing a set of specific oligonucleotide primers capable of specifically detecting SEQ ID NO: 1, 2, 3 or 4 for use in RT-PCR;

d. analyzing PCR product by electrophoresis or specific probe nucleotide sequence complementary to SEQ ID NO: 1, 2, 3 or 4.

The set of oligonucleotide primers of the invention are selected from

```
(i)   5' ATGCAGGTTGCGACTGTACACCCGG 3'
         (SEQ ID NO: 5)
      3' GGCCGCTCTTGTTCTTCGTCGGAT 5'
         (SEQ ID NO: 6)

(ii)  5' GTGTTTGCGTTGAGTAATAATCTGAACCGTGT 3'
         (SEQ ID NO: 7)
      3' AGCCAATTCCAGCACGATGTCGCC 5'
         (SEQ ID NO: 8)

(iii) 5' ATGCAGGTTGCGACTGTACACCCGG 3'
         (SEQ ID NO: 5)
      3' GGCCGCTCTTGTTCTTCGTCGGAT 5'
         (SEQ ID NO: 6)

(iv)  5' TGTACCGCGTGCCCGACGATTTG 3'
         (SEQ ID NO: 11)
      3' ACAGGCAGCTAACAGGGCGTCGG 5'
         (SEQ ID NO: 12)
```

(v) a set of oligonucleotide primers complementary to (i), (ii), (iii) or (iv) or (vi) a set of oligonucleotide primers comprising of sequence containing any 10 consecutive bases from one of the sequences selected from SEQ ID NO: 1, 2, 3 or 4.

In yet another aspect, the invention provides a kit for the detection of pathogenic *mycobacterium* sps in clinical samples, said kit comprising set of oligonucleotide primers selected from

```
(i)   5' ATGCAGGTTGCGACTGTACACCCGG 3'
      (SEQ ID NO: 5)
      3' GGCCGCTCTTGTTCTTCGTCGGAT 5'
      (SEQ ID NO: 6)

(ii)  5' GTGTTTGCGTTGAGTAATAATCTGAACCGTGT 3'
      (SEQ ID NO: 7)
      3' AGCCAATTCCAGCACGATGTCGCC 5'
      (SEQ ID NO: 8)

(iii) 5' ATGCAGGTTGCGACTGTACACCCGG 3'
      (SEQ ID NO: 5)
      3' GGCCGCTCTTGTTCTTCGTCGGAT 5'
      (SEQ ID NO: 6)

(iv)  5' TGTACCGCGTGCCCGACGATTTG 3'
      (SEQ ID NO: 11)
      3' ACAGGCAGCTAACAGGGCGTCGG 5'
      (SEQ ID NO: 12)
```

(v) a set of oligonucleotide primers complementary to (i), (ii), (iii) or (iv) or (vi) a set of oligonucleotide primers comprising of sequence containing any 10 consecutive bases from one of the sequences selected from SEQ ID NO: 1, 2, 3 or 4.

Furthermore, the invention provides a method of detecting pathogenic *mycobacterium* sps in a clinical sample wherein the sample is isolated from individuals vaccinated against tuberculosis.

It also provides a method of detecting pathogenic *mycobacterium* sps in a clinical sample wherein the sample is isolated from individuals treated against tuberculosis.

DETAILS OF THE INVENTION

The present invention relates to detection of pathogenic *Mycobacterium* species TABLE 1-continued Potential "signature sequences" carrying candidate genes

| H37Rv Gene Identifiers | Class | H37Rv protein description |
|---|---|---|
| Rv1991A | 2 | Antitoxin MazE6 |
| Rv2142A | 2 | Possible antitoxin ParD2 |
| Rv2231A | 2 | Possible toxin VapC16 |
| Rv2231B | 2 | Possible antitoxin VapB16 |
| Rv2274A | 2 | Possible antitoxin MazE8 |
| Rv2395A | 2 | Acid and phagosome regulated protein A AprA |
| Rv2395B | 2 | Acid and phagosome regulated protein B AprB |
| Rv2862A | 2 | Possible antitoxin VapB23 |
| Rv3190A | 2 | Hypothetical protein |
| Rv3344c | 2 | PE-PGRS family protein PE_PGRS49] [partial = 5'] |
| Rv3512 | 2 | PE-PGRS family protein PE_PGRS56] [partial = 5'] |
| Rv3599c | 2 | Hypothetical short protein |

In one aspect, the invention functionally characterizes the potential 'signature sequences (SS)'-carrying candidate genes based on functional information retrieved from Tuberculist (Tuberculosis (Edinb) 91, 7, 2011) and TB database (Nucleic Acids Research, 37, D499, 2009). Accordingly, the potential signature sequences can be functionally characterized into the following groups:

a. 9 (Rv0064A, Rv0456B, Rv0959A, Rv1991A, Rv2142A, Rv2231A, Rv2231B, Rv2274A and Rv2862A) fell into the toxin-antitoxin category.
b. 3 (Rv2653c, Rv2654c, Rv2658c) are possible prophages.
c. 2 (Rv3344c and Rv3512) belong to PE_PGRS family of proteins
d. 2 (Rv2645 and Rv2653c) are deleted (partially or completely) in one or more clinical isolates eliminating their use as diagnostic markers.
e. 9 (Rv1507A, Rv1509, Rv0078B, Rv2645, Rv0397A, Rv1366A, Rv1954A, Rv3599c, Rv3190A) are hypothetical proteins.
f. 2 (Rv2395A, Rv2395B) are acid and phagosome regulated proteins.

Based on the in-silico analysis, two Class 1 genes (Rv1507A and Rv1509) and two Class 2 genes (Rv1954A and Rv2231A) with homologs in *Mycobacterium bovis* BCG were selected as potential candidates (Table 2).

TABLE 2

Nucleotide Sequences of Potential "signature sequences" carrying genes

| Gene Name | Sequence | Description | Prediction Class |
|---|---|---|---|
| Rv1507A hypothetical protein | >Rv1507A<br>ATGCAATCAGGTCAAAATATCCTCGCCAAGGTATGTAATTT<br>GATTGAACAATCGCGACTTTCTTCAACGCGGTGTCTCCAAT<br>TTAGAATAACAAATACGTCGCGCCCGCGACAGCTCCGCTGG<br>AGCGAGTTCAAGCGATTCTGCGACATATTCAATATGGTGCT<br>CGGGAAGGCCAGGATGGGCCGCGACCCGGGGCGTCCGGTGC<br>GCGATGAACGTCGCATCGTCTCCTGTGAGATAATTGCATCC<br>GATCATATAGGGCTGGCTGCGGCTAGGTTGCTGGCAAAAAG<br>ATATCGCGGCCGATCCGTTTCTGGTTTTGTCTTGATGATCA<br>AATCCGCTTCCGTTCACGAGATCGATTCCTGGTCTTCCCCC<br>AGCGTCGCGATGTCGATAGGTGTCGCGCTTTGTTCGTACCC<br>GCACTACGCGGCGGCGAGAACCTCGCCACCGAATCGGGATT<br>GGGGGGAGGATACCACTCGGTCGAGGCCCGTCACCGGCCTT<br>CTAGCGGGTTG<br>(SEQ ID NO: 9) | Gene length: 504 bp,<br>Protein length: 167 aa | CLASS 1 |
| Rv1509Essential hypothetical protein | >Rv1509<br>GTGTTTGCGTTGAGTAATAATCTGAACCGTGTGAACGCATG<br>CATGGATGGATTCCTTGCCCGTATCCGCTCACATGTTGATG<br>CGCACGCGCCAGAATTGCGTTCACTGTTCGATACGATGGCG<br>GCCGAGGCCCGATTTGCACGCGCACTGGCTGTCCGAGGACC<br>TCGCGCGGTTGCCTGTCGGTGCAGCATTGCTGGAAGTGGGC<br>GGGGGGGTACTTCTGCTCAGCTGTCAACTGGCGGCGGAGGG<br>ATTTGACATCACCGCCATCGAGCCGACGGGTGAAGGTTTTG<br>GCAAGTTCAGACAGCTTGGCGACATCGTGCTGGAATTGGCT<br>GCAGCACGACCCACCATCGCGCCATGCAAGGCGGAAGACTT<br>TATTTCCGAGAAGCGGTTCGACTTCGCCTTCTCGCTGAATG<br>TGATGGAGCACATCGACCTTCCGGATGAGGCAGTCAGGCGG<br>GTATCGGAAGTGCTGAAACCGGGGGCCAGTTACCACTTCCT<br>GTGCCCGAATTACGTATTCCCGTACGAACCGCATTTCAATA<br>TCCCAACATTCTTCACCAAAGAGCTGACATGCCGGGTGATG<br>CGACATCGCATCGAGGGCAATACGGGCATGGATGACCCGAA<br>GGGAGTCTGGCGTTCGCTCAACTGGATTACGGTTCCCAAGG<br>TGAAACGCTTTGCGGCGAAGGATGCGACGCTGACCTTGCGC<br>TTCCACCGTGCAATGTTGGTATGGATGCTGGAACGCGCGCT<br>GACGGATAAGGAATTCGCTGGTCGCCGGGCACAATGGATGG<br>TCGCTGCTATTCGCTCGGCGGTGAAATTGCGTGTGCATCAT<br>CTGGCAGGCTATGTTCCCGCTACGCTGCAGCCCATCATGGA<br>TGTGCGGCTAACGAAGAGGTAA<br>(SEQ ID NO: 10) | Gene length: 882 bp,<br>Protein length: 293 aa | CLASS 1 |
| Rv1954a Hypothetical protein | >bi\|448814763: 2201231-2201623<br>*Mycobacterium tuberculosis* H37Rv<br>complete genome<br>TGGTATAAGCTGGTTTTAGACGAAAAGGACCCCACCTCGGG | Gene length: 303 bp,<br>Protein length 100 bp | CLASS 2 |

TABLE 2-continued

Nucleotide Sequences of Potential "signature sequences" carrying genes

| Gene Name | Sequence | Description | Prediction Class |
|---|---|---|---|
| | GTCTGATGGCCAGGGGCAGGGTCGTGTGCATTGGGGATGCA<br>GGTTGCGACTGTACACCCGGCGTGTTCCGCGCGACAGCGGG<br>TGGGATGCCGGTGCTGGTGGTCATCGAGTCTGGGACAGGAG<br>GTGATCAGATGGCTCGTAAAGCTACGTCCCCGGGTAAGCCG<br>GCTCCGACGTCGGGACAGTATCGCCCGGTTGGCGGTGGCAA<br>CGAGGTGACCGTTCCGAAGGGACACCGTCTGCCTCCCTCGC<br>CCAAGCCCGGTCAGAAGTGGGTGAACGTCGATCCGACGAAG<br>AACAAGAGCGGCCGCGGCTGAGCTTGTGCCGTCGGGATGGG<br>TGTCGCACCGTCTCGGCGGGTCGC<br>(SEQ ID NO: 13) | | |
| Rv2231A | >gi\|448814763: c2506224-2505671<br>Mycobacterium tuberculosis H37Rv<br>complete genome<br>GCCGCGGCGAGCCGGTAGCAAAGCTTGTGCCGCTGCATCCT<br>CATGAGACTCGGCGGTTAGGCATTGACCATGGCGTGTACCG<br>CGTGCCCGACGATTTGGACGCTCCGTTGTCAGACGACGTGC<br>TCGAACGCTTTCACCGGTGAAGCGCTACCTCATCGACACCC<br>ACGTTTGGCTGCGGATGCCGTCAACGAAACACGGGCGATTG<br>TTCAGGACGTCCGCAACAGCATTCTCTTGTCGGCCGCCAGT<br>GCCTGGGAGATCGCGATCAACTACCGCCTCGGCAAGCTCCC<br>GCCGCCCGAGCCATCGGCCTCTTACGTGCCCGATCGAATGC<br>GCCGCTGCGGCACGTCGCCGCTGTCAGTTGACCACGCACAC<br>ACTGCGCACCGCAGAGCTTCCGGATCACCATCGACATCCAT<br>TCGACCGTGTGCTCATCGCCCAGGCACAGCTGCTTGGCCTG<br>ACGATCATCACCGCCGACGCCCTGTTAGCTGCCTGTGATGT<br>CGCGGTTGTCGCCGCGTAGACAACGCGTCGGCGGTGCTCTG<br>GATTCTTGGCCCGCACACCG<br>(SEQ ID NO: 14) | Gene length: 426 bp,<br>Protein<br>length: 141 aa | CLASS 2 |

In a most preferred aspect, the signature sequences were designed keeping in view the diagnostic tool of RT PCR. These were short sequences amenable for PCR amplification from selected genes. The specific signature sequences, SS1 (Rv1507A), SS2 (Rv1509), SS3 (RV1954A) and SS4 (Rv2231A) of the invention are provided below. Homology search using NCBI nucleotide BLAST against the genus Mycobacterium was conducted on these signature sequences to confirm their uniqueness.

SS1 (Rv1507A): SEQ ID NO: 1
>Rv1507A
ATGCAATCAGGTCAAAATATCCTCGCCAAGGTATGTAATTTGATTGAAC

AATCGCGACTTTCTTCAACGCGGTGTCTCCAATTTAGAATAACAAATAC

GTCGCGCCCGCGACAGCTCCGCTGGAGCGAGTTCAAGCGATTCTGCGAC

ATATTCAATATGGTGCTCGGGAAGGCCAGGATGGGCCGCGACCCGGGGC

GTCCGGTGCGCGATGAACGTCGCATCGTCTCCTG 552 (Rv1509): SEQ ID NO: 2
>gi|448814763: 1700212-1701093
Mycobacterium tuberculosis H37Rv complete genome
GTGTTTGCGTTGAGTAATAATCTGAACCGTGTGAACGCATGCATGGATG

GATTCCTTGCCCGTATCCGCTCACATGTTGATGCGCACGCGCCAGAATT

GCGTTCACTGTTCGATACGATGGCGGCCGAGGCCCGATTTGCACGCGAC

TGGCTGTCCGAGGACCTCGCGCGGTTGCCTGTCGGTGCAGCATTGCTGG

AAGTGGGCGGGGGGGTACTTCTGCTCAGCTGTCAACTGGCGGCGGAGGG

ATTTGACATCACCGCCATCGAGCCGACGGGTGAAGGTTTTGGCAAGTTC

AGACAGCTTGGCGACATCGTGCTGGAATTGGCTGCA

SS3 (RV1954A): SEQ ID NO: 3
>gi|448814763: 2201277-2201579
Mycobacterium tuberculosis H37Rv complete genome
ATGGCCAGGGGCAGGGTCGTGTGCATTGGGGATGCAGGTTGCGACTGTA

CACCCGGCGTGTTCCGCGCGACAGCGGGTGGGATGCCGGTGCTGGTGGT

CATCGAGTCTGGGACAGGAGGTGATCAGATGGCTCGTAAAGCTACGTCC

CCGGGTAAGCCGGCTCCGACGTCGGGACAGTATCGCCCGGTTGGCGGTG

GCAACGAGGTGACCGTTCCGAAGGGACACCGTCTGCCTCCCTCGCCCAA

GCCCGGTCAGAAGTGGGTGAACGTCGATCCGACGA

SS4 (Rv2231A): SEQ ID NO: 4
>gi|448814763: c2506161-2505736
Mycobacterium tuberculosis H37Rv complete genome
TTGACCATGGCGTGTACCGCGTGCCCGACGATTTGGACGCTCCGTTGTC

AGACGACGTGCTCGAACGCTTTCACCGGTGAAGCGCTACCTCATCGACA

CCCACGTTTGGCTGCGGATGCCGTCAACGAAACACGGGCGATTGTTCAG

GACGTCCGCAACAGCATTCTCTTGTCGGCCGCCAGTGCCTGGGAGATCG

CGATCAACTACCGCCTCGGCAAGCTCCCGCCGCCCGAGCCATCGGCCTC

TTACGTGCCCGATCGAATGCGCCGCTGCGGCACGTCGCCGCTGTCAGTT

GACCACGCACACACTGCGCACCGCAGAGCTTCCGGATCACCATCGACAT

CCATTCGACCGTGTGCTCATCGCCCAGGCACAGCTGCTTGGCCTGA

For the purposes of PCR validation, the signature sequences SS1, SS2, SS3 and SS4 were selected and oligonucleotide primers were designed to generate corresponding specific PCR amplification products. Table 3 provides the set of designed oligonucleotide primers.

TABLE 3

Signature sequences SS1, SS2, SS3 and SS4 and respective oligonucleotide primers

| Signature Sequences (SS) | Sequence | Description | Prediction Class |
|---|---|---|---|
| SS1 from Rv1507A | >Rv1507A ATGCAATCAGGTCAAAATATCCTCGCCAAG GTATGTAATTTGATTGAACAATCGCGACTT TCTTCAACGCGGTGTCTCCAATTTAGAATA ACAAATACGTCGCGCCCGCGACAGCTCCGC TGGAGCGAGTTCAAGCGATTCTGCGACATA TTCAATATGGTGCTCGGGAAGGCCAGGATG GGCCGCGACCCGGGGCGTCCGGTGCGCGAT GAACGTCGCATCGTCTCCTG (SEQ ID NO: 1) | NZE_Rv1954A_F ATGCAGGTTGCGACTGTACACCCGG (SEQ ID NO: 5) Length = 25, Tm = 58.6, %G + C = 60 NZE_Rv1954A_R GGCCGCTCTTGTTCTTCGTCGGAT (SEQ ID NO: 6) Length = 24, Tm = 57.4, %G + C = 58.3 Amplicon Size = ~280 bp | CLASS 1 |
| SS2 from Rv1509 | >gi\|448814763: 1700212-1701093 *Mycobacterium tuberculosis* H37Rv complete genome GTGTTTGCGTTGAGTAATAATCTGAACCGT GTGAACGCATGCATGGATGGATTCCTTGCC CGTATCCGCTCACATGTTGATGCGCACGCG CCAGAATTGCGTTCACTGTTCGATACGATG GCGGCCGAGGCCCGATTTGCACGCGACTGG CTGTCCGAGGACCTCGCGCGGTTGCCTGTC GGTGCAGCATTGCTGGAAGTGGGCGGGGGG GTACTTCTGCTCAGCTGTCAACTGGCGGCG GAGGGATTTGACATCACCGCCATCGAGCCG ACGGGTGAAGGTTTTGGCAAGTTCAGACAG CTTGGCGACATCGTGCTGGAATTGGCTGCA (SEQ ID NO: 2) | NZE_Rv1509_F GTGTTTGCGTTGAGTAATAATCTGAACCGTGT (SEQ ID NO: 7) Length = 32, Tm = 57.5%G + C = 41 NZE_Rv1509_R AGCCAATTCCAGCACGATGTCGCC (SEQ ID NO: 8) Length = 24, Tm = 58.8, %G + C = 58.3 Amplicon size = ~330 bp | CLASS 1 |
| SS3 from Rv1954A | gi\|448814763: 2201277-2201579 *Mycobacterium tuberculosis* H37Rv complete genome ATGGCCAGGGGCAGGGTCGTGTGCATTGGG GATGCAGGTTGCGACTGTACACCCGGCGTG TTCCGCGCGACAGCGGGTGGGATGCCGGTG CTGGTGGTCATCGAGTCTGGGACAGGAGGT GATCAGATGGCTCGTAAAGCTACGTCCCCG GGTAAGCCGGCTCCGACGTCGGGACAGTAT CGCCCGGTTGGCGGTGGCAACGAGGTGACC GTTCCGAAGGGACACCGTCTGCCTCCCTCG CCCAAGCCCGGTCAGAAGTGGGTGAACGTC GATCCGACGA (SEQ ID NO: 3) | NZE_Rv1954A_F ATGCAGGTTGCGACTGTACACCCGG (SEQ ID NO: 5) Length = 25, Tm = 58.6, %G + C = 60 NZE_ Rv1954A_R GGCCGCTCTTGTTCTTCGTCGGAT (SEQ ID NO: 6) Length = 24, Tm = 57.4, %G + C = 58.3 Amplicon Size = ~280 bp | CLASS 2 |
| SS4 from Rv2231A | gi\|448814763: c2506161-2505736 *Mycobacterium tuberculosis* H37Rv complete genome TTGACCATGGCGTGTACCGCGTGCCCGACG ATTTGGACGCTCCGTTGTCAGACGACGTGC TCGAACGCTTTCACCGGTGAAGCGCTACCT CATCGACACCCACGTTTGGCTGCGGATGCC GTCAACGAAACACGGGCGATTGTTCAGGAC GTCCGCAACAGCATTCTCTTGTCGGCCGCC AGTGCCTGGGAGATCGCGATCAACTACCGC CTCGGCAAGCTCCCGCCGCCCGAGCCATCG GCCTCTTACGTGCCCGATCGAATGCGCCGC TGCGGCACGTCGCCGCTGTCAGTTGACCAC GCACACACTGCGCACCGCAGAGCTTCCGGA TCACCATCGACATCCATTCGACCGTGTGCT CATCGCCCAGGCACAGCTGCTTGGCCTGAC (SEQ ID NO: 4) | NZE_Rv2231A_F TGTACCGCGTGCCCGACGATTTG (SEQ ID NO: 11) Length = 23, Tm = 59.1, %G + C = 61 NZE_Rv2231A_R ACAGGCAGCTAACAGGGCGTCGG (SEQ ID NO: 12) Length = 23, Tm = 57.1, %G + C = 65 Amplicon Size = ~390 bp | CLASS 2 |

In a preferred embodiment, pathogenic *mycobacterium* sps can be detected with 100% specificity following PCR using DNA isolated from clinical samples from patients who presented with clinical symptoms of the disease. In another embodiment, pathogenic *mycobacterium* sps is also detected using the above method in clinical samples isolated from individuals vaccinated against tuberculosis. In yet another embodiment, pathogenic *mycobacterium* sps is also detected using the above method in clinical samples isolated from individuals treated against tuberculosis.

Pathogenic *mycobacterium* sps, as provided in the invention, includes *Mycobacterium tuberculosis* and *Mycobacterium bovis*. More specifically, pathogenic *mycobacterium* sps represents *Mycobacterium tuberculosis*, the TB causing bacterium.

Clinical samples, as meant here, includes specimens such as blood, sputum, cerebrospinal fluid, gastric lavage, tissue biopsies and the likes thereof. PCR product can be easily visualized by any conventional method that can be readily recognized by a person skilled in the art such as electrophoresis.

Following Examples serve as a tool to illustrate the invention. However, it should in no way be considered to be limiting the invention.

Example 1

Determination of Specificity and Sensitivity of Signature Sequences

Genomic DNA for PCR Amplification

Genomic DNA of *Mycobacterium tuberculosis* and 13 other mycobacterial species were used for testing the specificity of signature sequences using PCR. These include, *M. avium* subspecies *paratuberculosis, M. smegmatis* (ATCC19420), *M. vaccae, M. marinum* (ATCC927), *M. chelonae* (ATCC14472), *M. flavescens* (ATCC14474), *M. fortuitum* (ATCC6481), *M. kansasii* (ATCC12478), *M. bovis* (ATCC27294), *M. bovis* (BCG), *M. avium* (ATCC25291), *M. gastri, M. indicuspranii*.

PCR Reaction

The PCR reaction mixture (50 μl) consisted of 10×taqPCR buffer, 0.5 mmolMgCl2, 0.4 mmol dNTP, 10 pmol forward and reverse primers respectively, 4% DMSO and 1 Utaq DNA polymerase. The reaction conditions were the following: 95° C. for 5 minutes, followed by 35 cycles of 95° C. for 30 seconds, annealing temperature 50° C. for 30 seconds, 72° C. for 1 minute and finally 72° C. for 10 minutes. All PCR products were electrophoresed on 2% agarose gel with ethidium bromide staining.

The "signature sequences" were tested for their ability to differentiate *Mycobacterium tuberculosis* DNA from a large number of other mycobacterial DNA in PCR using primers complementary to these "signature sequences" as shown in Table 3. For this purpose, chromosomal DNA extracted from 13 *mycobacterium* species including human genomic DNA were tested by *mycobacteruim* genus-specific primers of the 'signature sequences'. SS1 and SS2 were negative for all 13 *mycobacterium* species tested whereas SS3 and SS4 show positive PCR results only when *M. bovis* BCG genomic DNA was used as template.

Table 4 summarizes the specificity data resulting from PCR using specific primers of signature sequences SS1, SS2, SS3 and SS4.

TABLE 4

Specific amplification of signature sequences from *Mycobacterium tuberculosis* and *M. bovis* BCG

| Specimen | SS1 | SS2 | SS3 | SS4 |
|---|---|---|---|---|
| M. tuberculosis | + | + | + | + |
| M. bovis BCG | − | − | + | + |
| M. avium | − | − | − | − |
| M. smegmatis | − | − | − | − |
| M. vaccae | − | − | − | − |
| M. chelonae | − | − | − | − |
| M. flori | − | − | − | − |
| M. fortuitum | − | − | − | − |
| M. kansasi | − | − | − | − |
| M. bovis | − | − | − | − |
| M. marinum | − | − | − | − |
| M. gastri | − | − | − | − |
| MIP | − | − | − | − |
| MAP | − | − | − | − |
| M. leprae | | | | |
| Human Genome | − | − | − | − |

Furthermore, sensitivity analysis revealed that the signature sequences were highly sensitive in being able to detect <1 ng (100 pg) DNA as shown in FIGS. 1A, 1B, 1C and 1D for the four primers of the signature sequences SS1, SS2, SS3 and SS4 respectively.

Example 2

Evaluation of *Mycobacterium tuberculosis*-Specific Primer Pair Using Clinical Samples A) Amplification of Signature Sequences from Patient Sputum Samples Sputum samples were processed by the Universal Sample Processing (USP) method for DNA extraction as described by Chakravorty et al (J Clin Microbiol 43, 4357, 2005). DNA was isolated from the USP sediments by boiling in the presence of five volumes of solution containing 10% Chelex-100 resin, 0.03% triton X-100, and 0.3% Tween 20. The isolated DNA was stored at 20° c. and used for PCR assay.

PCR reaction was carried out using specific primers as given in Table 3.

Figure 1A:
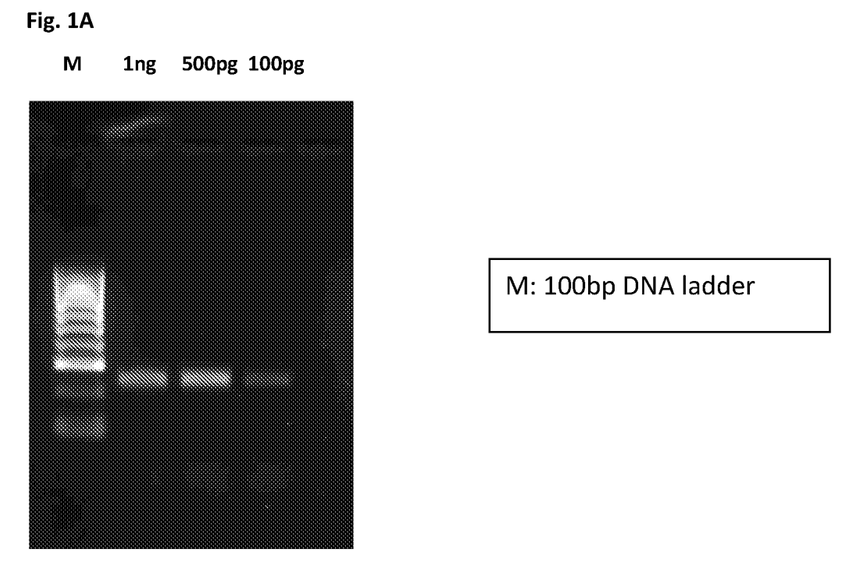
FIG. 1A: Amplification of SS1 at low and varied DNA template concentrations.
Figure 1B:
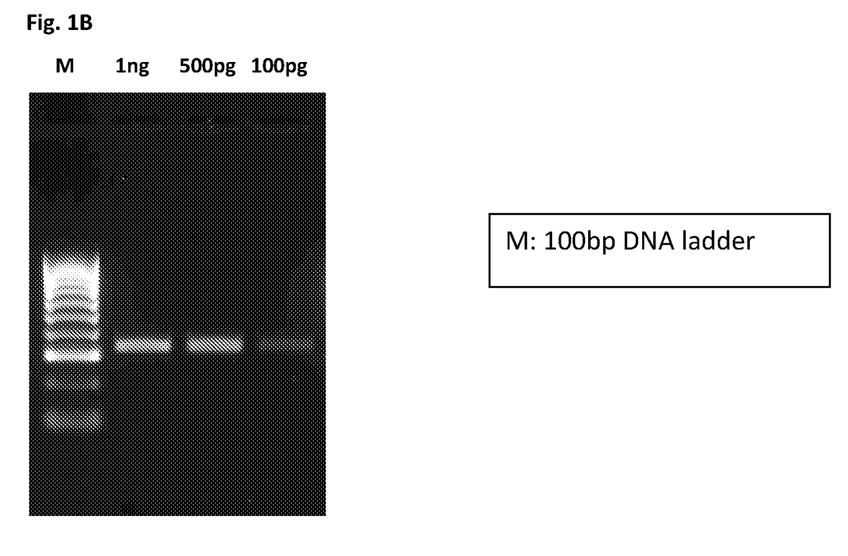
FIG. 1B: Amplification of SS2 at low and varied DNA template concentrations.
Figure 1C:
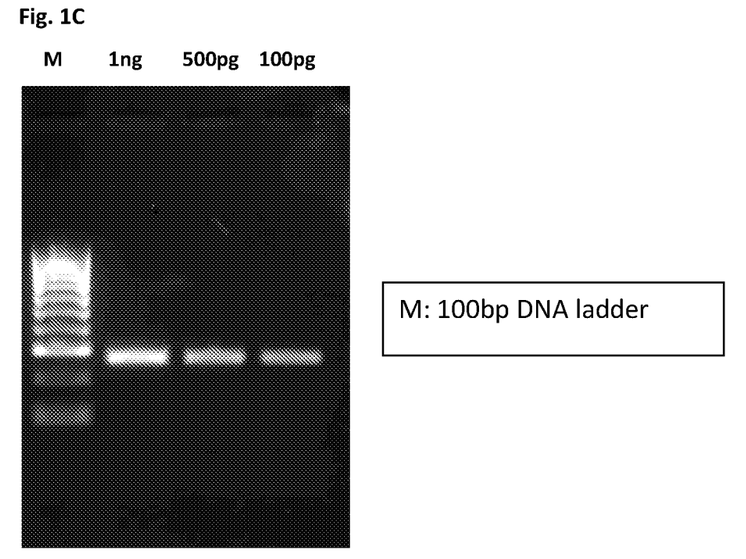
FIG. 1C: Amplification of SS3 at low and varied DNA template concentrations.
Figure 1D:
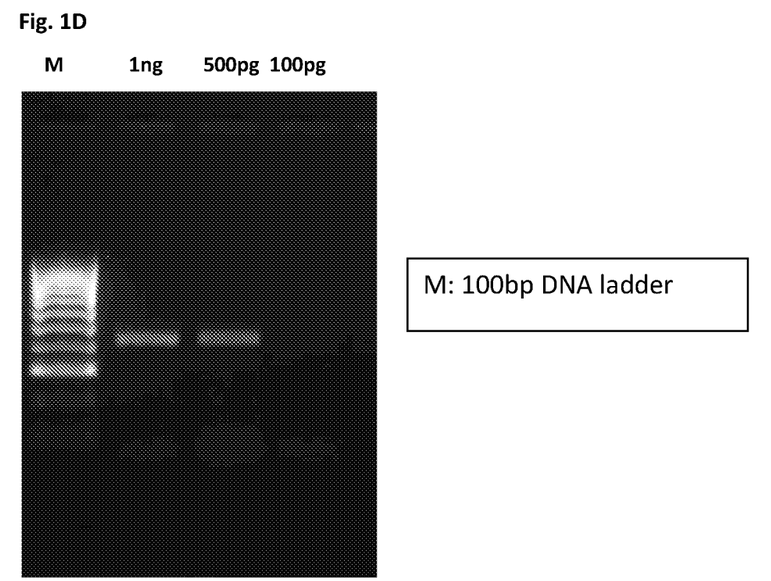
FIG. 1D: Amplification of SS4 at low and varied DNA template concentrations.
Figure 2:
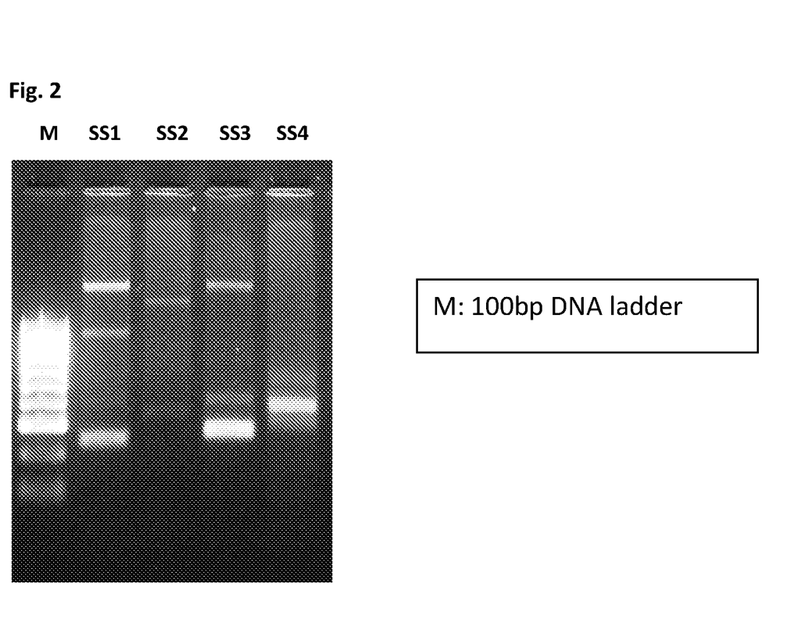
FIG. 2: Amplification of signature sequences SS1, SS2, SS3 and SS4 from patient sputum samples.

The results show amplification of signature sequences in patient sputum sample (FIG. 2) demonstrating the diagnostic utility of the signature sequences for detecting pathogenic *Mycobacterium tuberculosis*.

B) Amplification of Signature Sequences from Patient Blood Samples

DNA from blood samples of tuberculosis patients were isolated as per the protocol described in van Helden et al (Isolation of DNA from *Mycobacterium tuberculosis*, Paul D. van Helden, Thomas C. Victor, Robin M. Warren, and Eileen G. van Helden)

Figure 3:
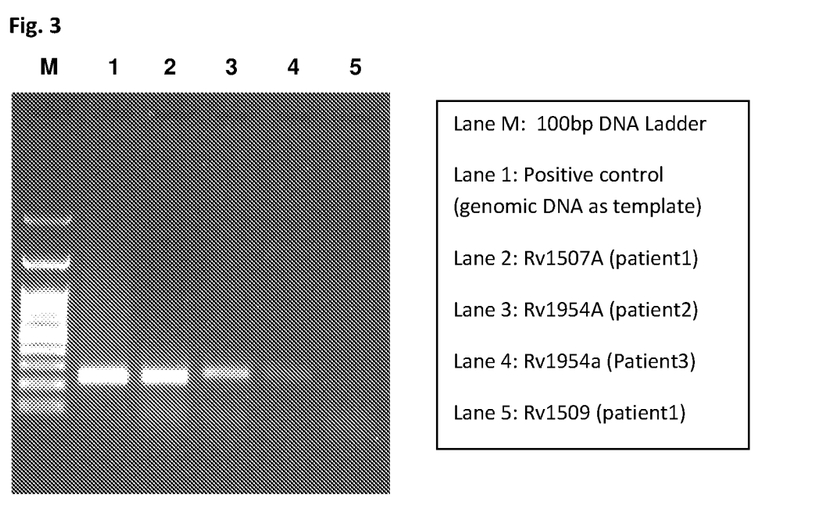
FIG. 3: Amplification of signature sequences SS1 and SS3 from patient blood samples.

The results show amplification of SS1 and SS3 as seen in FIG. 3.

We claim:

1. A method of detecting *Mycobacterium tuberculosis* in a clinical sample, said method comprising the steps of:
    a) removal of contaminants from the clinical sample to generate a contaminant-free clinical sample;
    b) extraction of genomic DNA from the contaminant-free clinical sample;
    c) designing a set of specific oligonucleotide primers that amplify a nucleic acid consisting of SEQ ID NO: 1 for use in RT-PCR;
    d) performing PCR with the oligonucleotide primers of step c) on the genomic DNA of step b) to produce a PCR product; and
    e) analyzing the PCR product obtained in step d) by electrophoresis or specific probe nucleotide sequence complementary to SEQ ID NO: 1.

2. The method of claim 1, wherein the set of oligonucleotide primers are selected from:

```
(i)  5' ATGCAGGTTGCGACTGTACACCCGG 3'
     (SEQ ID NO: 5)
     3' GGCCGCTCTTGTTCTTCGTCGGAT 5';
     (SEQ ID NO: 6)
```

(ii) a set of oligonucleotide primers complementary to (i); or (iii) a set of oligonucleotide primers comprising a sequence containing any 10 consecutive bases from the sequence of SEQ ID NO: 1.

3. The method of claim 1, wherein the clinical sample is isolated from individuals vaccinated against tuberculosis.

4. The method of claim 1, wherein the clinical sample is isolated from individuals treated against tuberculosis.

* * * * *

UNITED STATES PATENT AND TRADEMARK OFFICE
CERTIFICATE OF CORRECTION

PATENT NO. : 10,597,734 B2
APPLICATION NO. : 15/100850
DATED : March 24, 2020
INVENTOR(S) : Rahman et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 316 days.

Signed and Sealed this
Seventh Day of February, 2023

Katherine Kelly Vidal
*Director of the United States Patent and Trademark Office*